(12) United States Patent
Perraut et al.

(10) Patent No.: US 9,046,487 B2
(45) Date of Patent: Jun. 2, 2015

(54) DEVICE FOR LIGHTING AN OBJECT, WITH LIGHT SOURCE PROVIDED WITH A MEMBER FOR SAMPLING A PORTION OF SAID LIGHT, APPLICATION TO THE MEASUREMENT OF FLUX VARIATIONS OF THE SOURCE

(75) Inventors: Francois Perraut, Saint Joseph de Riviere (FR); Thierry Flahaut, Chollonge (FR)

(73) Assignee: Commissariat à l'énergie atomique et aux énergies alternatives, Paris (FR)

(*) Notice: Subject to any disclaimer, the term of this patent is extended or adjusted under 35 U.S.C. 154(b) by 175 days.

(21) Appl. No.: 13/591,524

(22) Filed: Aug. 22, 2012

(65) Prior Publication Data

US 2013/0056620 A1    Mar. 7, 2013

(30) Foreign Application Priority Data

Sep. 2, 2011  (FR) .................................... 11 57811

(51) Int. Cl.
*H04N 5/262* (2006.01)
*G01N 21/64* (2006.01)
*G01N 21/78* (2006.01)

(52) U.S. Cl.
CPC .............. *G01N 21/645* (2013.01); *G01N 21/78* (2013.01)

(58) Field of Classification Search
CPC ................................ H04N 5/361; H04N 5/378
USPC ....................... 250/208.1, 205; 353/31, 69, 94
See application file for complete search history.

(56) References Cited

U.S. PATENT DOCUMENTS

| | | |
|---|---|---|
| 5,779,978 A | 7/1998 | Hartmann et al. |
| 6,511,222 B1 | 1/2003 | Bouamra et al. |
| 6,614,215 B1 | 9/2003 | Wood |
| 6,775,001 B2 | 8/2004 | Friberg et al. |
| 7,052,138 B2 * | 5/2006 | Matsui ............................ 353/31 |
| 7,064,893 B2 | 6/2006 | Boutet et al. |
| 7,911,700 B2 | 3/2011 | Chao et al. |
| 8,173,440 B2 | 5/2012 | Paolacci et al. |
| 8,199,328 B2 | 6/2012 | Goldberg et al. |
| 8,654,319 B2 | 2/2014 | Rao et al. |
| 2004/0008393 A1 | 1/2004 | Matsushita et al. |
| 2004/0252943 A1 | 12/2004 | Schilling |
| 2006/0289787 A1 | 12/2006 | Ohman et al. |

(Continued)

FOREIGN PATENT DOCUMENTS

| | | |
|---|---|---|
| EP | 2 423 668 A1 | 2/2012 |
| WO | WO 2004/055502 A2 | 7/2004 |

(Continued)

OTHER PUBLICATIONS

U.S. Appl. No. 13/596,485, filed Aug. 28, 2012, Perraut et al.

(Continued)

*Primary Examiner* — Tony Ko
(74) *Attorney, Agent, or Firm* — Oblon, McClelland, Maier & Neustadt, L.L.P.

(57) ABSTRACT

A device for lighting an object, with light source provided with a member for sampling a portion of the light, application to the measurement of flux variations of the source. The device includes at least one light source emitting an illuminating light around an illumination axis, for lighting the object, and a photodetector.

12 Claims, 11 Drawing Sheets

(56) References Cited

U.S. PATENT DOCUMENTS

2009/0091837 A1 4/2009 Chao et al.
2012/0113421 A1 5/2012 Vignoud et al.

FOREIGN PATENT DOCUMENTS

WO WO 2004/055502 A3 7/2004
WO WO 2006/135306 A1 12/2006
WO WO 2007/031657 A2 3/2007

OTHER PUBLICATIONS

Search Report issued Mar. 15, 2012 in French Application No. 1157811 (With English Translation of Category of Cited Documents).
E. Schultz, et al., "A novel fluorescence-based array biosensor: Principle and application to DNA hybridization assays", Biosensors and Bioelectronics, vol. 23, 2008, pp. 987-994.
Romain Dagnelie, et al., "Méthodes de Mesure du Formaldéhyde dans L'Atmosphere", Revue Air Pur No. 74, Premier Semestre, 2008, pp. 14-21.
J. M. Elson, et al., "Relationship of the total integrated scattering from multiplayer-coated optics to angle of incidence, polarization, correlation length, and roughness cross-correlation properties", Applied Optics, vol. 22, No. 20, Oct. 15, 1983, pp. 3207-3219.
Edina Németh, et al., "Real-time study of the effect of different stress factors on lactic acid bacteria by electrochemical optical waveguide lightmode spectroscopy", Biomolecular Engineering, vol. 24, 2007, pp. 631-637.
Yuan-Yu Lin, et al., "Integration of polymer light-emitting diode and polymer waveguide on Si substrate", Applied Physics Letters, vol. 89, 2006, pp. 063501-1 to 063501-3.
European Search Report issued Oct. 25, 2012 in Patent Application No. EP 12 18 2120 (with English translation of categories of cited documents).

* cited by examiner

DEVICE FOR LIGHTING AN OBJECT, WITH LIGHT SOURCE PROVIDED WITH A MEMBER FOR SAMPLING A PORTION OF SAID LIGHT, APPLICATION TO THE MEASUREMENT OF FLUX VARIATIONS OF THE SOURCE

CROSS-REFERENCE TO RELATED APPLICATION

This application is based upon and claims the benefit of priority under 35 U.S.C. §119 from prior French Patent Application No. 11 57811, filed on Sep. 2, 2011. The entire content of the above application is incorporated herein by reference.

TECHNICAL FIELD

The present invention relates to a device for lighting an object.

It applies in particular to all fields in which is used a light source in which it is wished to correct variations of luminous flux.

For example, the device, the subject matter of the invention, may be used in a photometer, a spectrophotometer, a fluorometer, a spectrofluorometer, a microscope, a scanner, and a device for lighting a scene (the latter then constituting the object).

Said device may more particularly be used in all optical measurement instruments for which the result of the measurement depends on the flux of a source known as "excitation source" or "illumination source", for example an absorption or fluorescence photometer.

More generally, said device may be used with any optical measurement instrument intended to carry out transmission, absorption, reflection, scattering, or fluorescence measurements, in spectrometric mode or not.

Said device may in particular be used in the case where it is wished to perform the regulation of the flux of a light source, for example in a device for detecting and assaying biological or chemical substances, contained in a fluid (liquid or gas).

PRIOR ART

FIG. 1 is a schematic view of a known device for measuring the variations of luminous flux of a light source 2, forming part of a device 4. Said device comprises a beam splitter 6 and a photodetector 8.

The beam splitter 6 transmits a small portion of the light emitted by the source 2 to the photodetector 8; and the major part of said light is used by another component 10 of the device 4.

Thus it is possible to measure any variation of luminous flux of the source 2 by the photodetector 8.

Another known device (FIG. 2) uses simply the photodetector 8. The latter is placed in the vicinity of the source 2 and makes it possible to measure a portion of the light emitted by the source 2 but not used by the other component 10 of the system 4.

When a fluorescence measurement is performed, the fluorescence emission flux depends on the excitation flux. And the relation linking the latter with the fluorescence emission flux depends on the properties of the sensitive material used for the measurement.

A very thin layer of sensitive material may be used. This is typically the case of biochips for which the distribution of fluorophores is equivalent to a monomolecular film.

In this case, the relation that links the fluorescence emission flux $F_{em}$ to the excitation flux $F_{ex}$ is the following:

$$F_{em}=D_{Pex}\cdot\sigma_a\cdot QE_f\Gamma_f S \propto D_{Pex}\cdot S \propto F_{ex} \qquad (1)$$

The symbols used in this relation have the following significations:

$D_{Pex}$ (in W/m²): power density measured after the excitation filter that is used for the measurement;

$\sigma_a$ (in m): maximum cross section, given by the supplier of the sensitive material, or calculated from the molar extinction coefficient;

$QE_f$: emission quantum efficiency of the fluorescent markers;

$\Gamma_f$ (in m⁻²): density of the fluorophores,

S (in m²): illuminated surface of the sensitive material; and $\propto$: symbol reflecting a relation of proportionality.

For the relation (1), it is considered that the light source used emits the same energy at all wavelengths and that the cross section and the quantum efficiency are constant for all wavelengths.

It is pointed out that this approximation does not have an incidence on the present invention.

The layer of sensitive material used may be thicker. This is for example the case for certain materials that are sensitive to chemical compounds (for example polymers or sols-gels) or liquid solutions.

The phenomenon of light absorption is then well described by the Beer-Lambert law:

$$I_a = I_0 \cdot \exp(-\epsilon \cdot l \cdot c) \propto I_0 \qquad (2)$$

where $I_0$ represents the intensity of the light that is received by the sensitive material, and $I_a$ represents the intensity of the light absorbed by the latter.

The emitted fluorescence may then be described by the following relation:

$$F_{em} = F_{ex} \cdot \exp(-\epsilon \cdot l \cdot c) \cdot QE_f \propto F_{ex} \qquad (3)$$

The symbols $\epsilon$, l, c used in said relations have the following significations:

$\epsilon$ (in l·mol⁻¹·cm⁻¹): molar extinction coefficient;

l (in cm): thickness of the material; and c (in mol): concentration of fluorophore in the material.

For the relations (2) and (3), the same approximation on wavelengths as for the relation (1) has been applied.

Moreover, the relation (2) applies to a transmission measurement: the information, or "specific signal", is obtained by measuring the attenuation of the light when it traverses the studied medium.

The relations (1), (2) and (3) show that any variation in the light flux of the source entails a linear variation of said flux, whether it is determined by a fluorescence, transmission, scattering, or reflection measurement.

Said variation of the light flux of the source causes a bias for the measurements. If it is not corrected, said bias introduces a noise in said measurements and reduces the performances of the instrument used for them.

The two techniques for sampling a portion of the flux of the source, which have been described with reference to FIGS. 1 and 2, are not adapted to a device for detecting and assaying biological or chemical substances, contained in a liquid or a gas, such as the device that is described in the following document, to which reference will be made:

[1] E. Schultz et al., Biosensors and Bioelectronics, vol. 23 (2008), pages 987 to 994.

FIG. 3A is a schematic sectional view of said device; and FIG. 3B is a schematic top view thereof.

Hereafter, the constitution and the functioning of the device that is represented in FIGS. 3A and 3B is briefly described.

It comprises a transparent support 12, in plate form, for example made of glass, silica, quartz, or plastic. On separate parts of the upper face 13 of said support 12, known as "interrogation areas", are available respectively different materials, known as sensor materials, which are sensitive to compounds of biological or chemical origin.

Said sensor materials are fluorescent and their fluorescence properties are modified when they are exposed to the compounds that it is wished to detect or assay.

In FIG. 3A, only the sensor materials $14_1$, $14_2$, $14_3$ and the corresponding interrogation areas $z_1$, $z_2$, $z_3$ are represented; and, in FIG. 3B, the sensor materials $14_1$ to $14_6$ are represented.

The sensor materials are exposed to a liquid or gaseous sample E that is liable to contain the compounds that it is wished to detect or assay.

To do this, the support 12 is optionally placed in a circulation chamber 16 provided with an inlet port 18 and an outlet port 20 enabling respectively the introduction of the sample in the circulation chamber 16 and the evacuation of the sample therefrom.

In the device that is represented in FIGS. 3A and 3B, the circulation chamber 16 rests on the upper face of the support 12, as may be seen; and FIG. 3B is a top view of the device stripped of the circulation chamber.

Said device also comprises light sources that are respectively placed facing the interrogation areas, under the lower face 22 of the transparent support 12.

In FIG. 3A, only the light sources $24_1$, $24_2$, $24_3$ that correspond respectively to the interrogation areas $z_1$, $z_2$, $z_3$ are represented.

The excitation light, coming from each source, is optically shaped through the intermediary, successively, of a first lens, a filter making it possible to select an optimal spectral interval, and a second lens.

In FIG. 3A are only represented:
the lenses $26_1$, $26_2$, $26_3$ which are respectively situated facing the sources $24_1$, $24_2$, $24_3$,
the filter 28 that follows said lenses, and
the lenses $30_1$, $30_2$, $30_3$ which follow the filter that follows the filter 28.

As may be seen, each lens-filter-lens assembly, such as the lens $26_1$-filter 28-lens $30_1$ assembly, is respectively associated with one of the sources, such as the source $24_1$, and is placed facing the support 12.

It is nevertheless pointed out that the means (lenses and filter) for shaping the excitation light are optional.

Moreover, a photodetector 32 is placed in front of one 34 of the sides of the support 12; and a filter 36 is optionally placed between this side 34 and the photodetector 32.

The reading of the support 12, comprising the interrogation areas, is performed by switching on then switching off the light sources one after the other, and by synchronising the switching on-switching off of each source with the measurement of the fluorescence flux emitted by the corresponding interrogation area.

Appropriate means (not represented) are provided to control the successive switchings on-switchings off, by synchronizing the measurements with these.

The photodetector 32 (which performs the measurements) supplies electrical signals, representative of the luminous fluxes successively reaching it, to appropriate electronic processing means (not represented).

The fluorescence light is conducted, by total reflection, up to the side 34 of the support 12, then detected by the photodetector 32.

The device of FIGS. 3A and 3B thus makes it possible to interrogate several interrogation areas by successively switching on separate light sources.

FIG. 4 illustrates schematically a technique for sampling a portion of the flux of each light source: each source is associated with a beam splitter and an auxiliary photodetector, or reference photodetector.

In FIG. 4 are simply represented the beam splitters $38_1$, $38_2$ and the auxiliary photodetectors $40_1$, $40_2$.

As may be seen, the beam splitter $38_1$ (or $38_2$) is arranged behind the source $24_1$ (or $24_2$) but before the lens $26_1$ (or $26_2$), when the latter exists, and reflects a part of the light emitted by the source $24_1$ (or $24_2$) in the direction of the auxiliary photodetector $40_1$ (or $40_2$).

Nevertheless, such a set of beam splitters-auxiliary photodetectors is bulky and difficult to put in place. In addition, the technique illustrated by FIG. 4 requires physically multiplexing the reference measurements.

It should be recalled that said reference measurements make it possible to know the flux variations of the various sources of light, for example with a view to regulating said sources so that they each emit a substantially constant flux.

FIG. 5 schematically illustrates another technique for sampling a portion of the flux of each light source: an auxiliary photodetector is placed on the optical axis corresponding to said source, above the circulation chamber, or reaction chamber; and a transparent window is provided in the wall of the chamber, on the optical axis.

In FIG. 5 are only represented the auxiliary photodetectors $42_1$, $42_2$, $42_3$, the optical axes $X_1$, $X_2$, $X_3$ and the windows $44_1$, $44_2$, $44_3$ which are respectively associated with the sources $24_1$, $24_2$, $24_3$.

As an example, it may be seen that the light emitted by the source $24_1$, along the axis $X_1$, traverses the plate 12, interacts with the material $14_1$, traverses the window $44_1$ and reaches the auxiliary photodetector $42_1$.

Such a device induces strong constraints on the circulation chamber: as in the case of the example illustrated by FIG. 4, it is necessary to have as many auxiliary photodetectors, or reference photodetectors, as light sources; moreover, it is necessary to physically multiplex the reference measurements.

FIG. 6 schematically illustrates a variant of FIG. 5, according to which a portion of the light reflected by the lower face 22 of the transparent support is measured by means of a pair of auxiliary photodetectors, or reference photodetectors.

The latter are provided, in addition to sources, in the lighting means 46 comprising the sources and the optional means for shaping the light emitted by said sources.

In FIG. 6 are simply represented the pair of reference photodetectors $C_2$, $D_2$ which are associated with the source $24_2$ and placed at the level of the corresponding lens $30_2$, on either side thereof, facing the face 22 of the plate 12.

This other technique also necessitates having several reference photodetectors, and thus a more complex lighting system, as well as a physical multiplexing of the reference measurements.

To reduce the number of reference photodetectors, it is possible to place a single reference photodetector in front of one of the sides of the transparent support 12, other than the side 34 in front of which is already placed the photodetector 32.

This is schematically illustrated by FIG. 7 which shows a reference photodetector 47 placed in front of the side 37 of the transparent support 12, opposite to the side 34. The reference measurement is made, by the photodetector 47, in the same way as the fluorescence measurement performed by the photodetector 32.

Compared to the preceding configurations, the configuration of FIG. 7 has the advantage of being easy to implement. Moreover, it only requires a single photodetector to carry out the reference measurement and thereby avoids physical multiplexing.

However, the optical power measured in the configuration of FIG. 7 is very low. This imposes the use of a very sensitive photodetector, of the photomultiplying tube or avalanche photodiode kind. But these two types of photodetectors are costly.

For example, measurements have been carried out by means of light sources $24_1$, $24_2$, ... of Luxeon® III Emitter Lambert LXHL-PM09 type, supplied by a current of 350 mA.

The light emitted by said sources has been shaped by bead lenses of 5 mm diameter $26_1$, $26_2$, ..., $30_1$, $30_2$, ... of Melles Griot 06LMS005 type, through a interferential filter 28 of Omega® Optical 525AF45/25R type.

The energy excitation has been measured with an amplified photodetector of Hamamatsu H8249-101 type. A value of 50 pW/mm² for a circulation chamber 16 filled with gas, and a value of 42 pW/mm² for a circulation chamber filled with liquid have been found.

If a conventional photodiode is used, having a detectivity of 0.2 A/W and a surface of 0.5 mm² to measure the flux of light, a current I of the order of 5 pA is obtained.

The Schottky noise $\sigma_S$, linked to the generation of such a current by a photodiode, is given by the following equation:

$$\sigma_S = \sqrt{\frac{2 \cdot e \cdot I}{\Delta t}} \quad (4)$$

In this equation, $\sigma_S$ represents the amplitude of the Schottky noise (in amperes), e the electron charge ($1.6 \times 10^{-19}$ C) and $\Delta t$ the time measurement (in seconds).

The Schottky noise is of the order of 160 fA for a measurement time of 50 μs, hence a relative uncertainty Inc % of three standard deviations of 12%, according to the following equation:

$$Inc \% = \frac{3 \cdot \sqrt{\frac{2 \cdot e \cdot I}{\Delta t}}}{I} \cdot 100 \quad (5)$$

Such a relative uncertainty is bothersome for low flux fluorescence measurements, which is generally the case of any fluorescence measurement.

Typically, the uncertainties of the measurements carried out with the device that is described in the document [1] are of the order of 1% for an interrogation time of 300 ms for each area.

Correcting the time variations of the flux of sources by measurements in which the noise is, in a relative manner, much greater than the noise of the studied phenomenon, leads to a degradation of performance, which is contrary to the sought for effect.

To reduce said noise, it is possible (1) to increase the measurement time, by integrating the current, or (2) to carry out several averaged elementary measurements. Nevertheless, these two methods lead to an increase in the interrogation time of each area.

For example, by ignoring the noises specific to the electronic circuit for measuring the current of the photodiode, it may be shown that the method (2) imposes making 14400 elementary measurements to obtain a relative uncertainty of 0.1%, hence an interrogation time increased by 720 ms, with a measurement time of 50 μs. This comes down to tripling the interrogation time.

If the measurement time $\Delta t$ is increased by means of a suitable electronic circuit, a relative uncertainty of 0.1% for a measurement time of 350 ms is theoretically attained, hence a pass band of the circuit less than 3 Hz. In the latter case, the interrogation time is doubled.

DESCRIPTION OF THE INVENTION

The aim of the present invention is to overcome the preceding drawbacks.

It relates to a device for lighting an object, comprising a light source, particularly a device of the kind of those that have been described above, comprising a light source intended to light a sample.

Said device comprises a means for sampling and guiding light.

In a preferred embodiment,
said means make it possible to work with a single reference photodetector, which avoids physical multiplexing of the measurements;
the insertion of the means in the lighting device is simple and easy; and
said means make it possible to obtain, upstream of the reference photodetector, a sufficiently high reference flux so that the measurement uncertainty obtained is low compared to the uncertainty of a fluorescence measurement.

In a precise manner, the present invention relates to a device for lighting at least one object, said device comprising at least one light source, emitting an illuminating light around an illumination axis, for lighting said object, and a photodetector, the device moreover comprising a means for sampling and guiding light, arranged upstream of the object, said sampling and guiding means being able to deviate and guide a part of said illuminating light, characterized in that it comprises:
a first photodetector for receiving the light transmitted by the object under the effect of the illumination,
a reference photodetector for receiving the light guided by the means for sampling and guiding light, and
a means for processing the signal supplied by the photodetector by means of the signal supplied by the reference photodetector.

According to a preferred embodiment of the device, the subject matter of the invention, the means for sampling and guiding light comprises a plate with parallel faces that is transparent in the spectral domain of the illuminating light.

Preferably, the means for sampling and guiding light is oriented perpendicularly to the lighting axis, so as to guide the light deviated perpendicularly to the lighting axis.

According to a particular embodiment of the device, the subject matter of the invention, the light source is provided with an optical system to shape the emitted light, said optical system comprising successively, from the light source, a first lens, a wavelength filter and a second lens, and the plate with parallel faces is arranged in one of the places chosen among:
a place between the light source and the first lens,
a place between the first lens and the wavelength filter,
a place between the wavelength filter and the second lens, and
a place behind the second lens.

According to a preferred embodiment of the invention, the plate with parallel faces comprises at least one light scattering area, which is able to deviate the light emitted by the source such that the deviated light is guided by said plate with parallel faces.

According to a first particular embodiment of the invention, the light scattering area has the shape of a ring.

According to a second particular embodiment, the light scattering area has the shape of a disc.

Preferably, the light scattering area is a superficial rough area of the plate with parallel faces.

The arithmetic roughness of the superficial rough area is preferably greater than the wavelengths of the spectral domain to which belongs the light emitted by the source. Said arithmetic roughness is then comprised in the interval ranging from 100 nm to 50 μm.

The plate with parallel faces may comprise two light scattering areas which are identical or, quite the opposite, different, and which are respectively situated facing each other, on two opposite faces of the plate with parallel faces.

According to a preferred embodiment of the invention, the thickness of the plate with parallel faces is comprised in the interval ranging from 50 μm to 5 mm, preferably from 500 μm to 2 mm.

The present invention also relates to a method for correcting an optical signal emitted by an object, comprising the following steps:
  lighting the object by means of a light source,
  detecting the light emitted by the object under the effect of the illumination by the light source, by means of a first photodetector,
  deviating the light emitted by the source, upstream of the illuminated object, by means of a light guide, the latter guiding the light deviated to a reference photodetector, and
  processing the signal produced by the first photodetector as a function of the signal detected by the reference photodetector.

Preferably, the processing comprises a correction of the signal produced by the first photodetector as a function of the signal detected by the reference photodetector.

BRIEF DESCRIPTION OF DRAWINGS

The present invention will be better understood on reading the description of embodiment examples given hereafter purely for illustration purposes and in no way limiting, by referring to the appended drawings in which.

DETAILED DESCRIPTION OF SPECIFIC EMBODIMENTS

Apart from certain lasers, the emission of luminous sources is not very directive: it does not take place along a single angle but along different angles. And the angular distribution of the light emission depends on the type of source considered (for example filament source, semiconductor source, or arc source) and the type of optic associated with the source.

For example, numerous light emitting diodes are equipped with a lens that is directly fixed to the support in which said diodes are provided, in order to condition the light emitted. And certain arc or filament lamps are equipped with a mirror making it possible to redirect the light emitted by such sources to the rear thereof, in the opposite direction.

In all cases, the output beam of such sources is little collimated: the light rays composing said beam are not parallel with each other.

Figure 8:
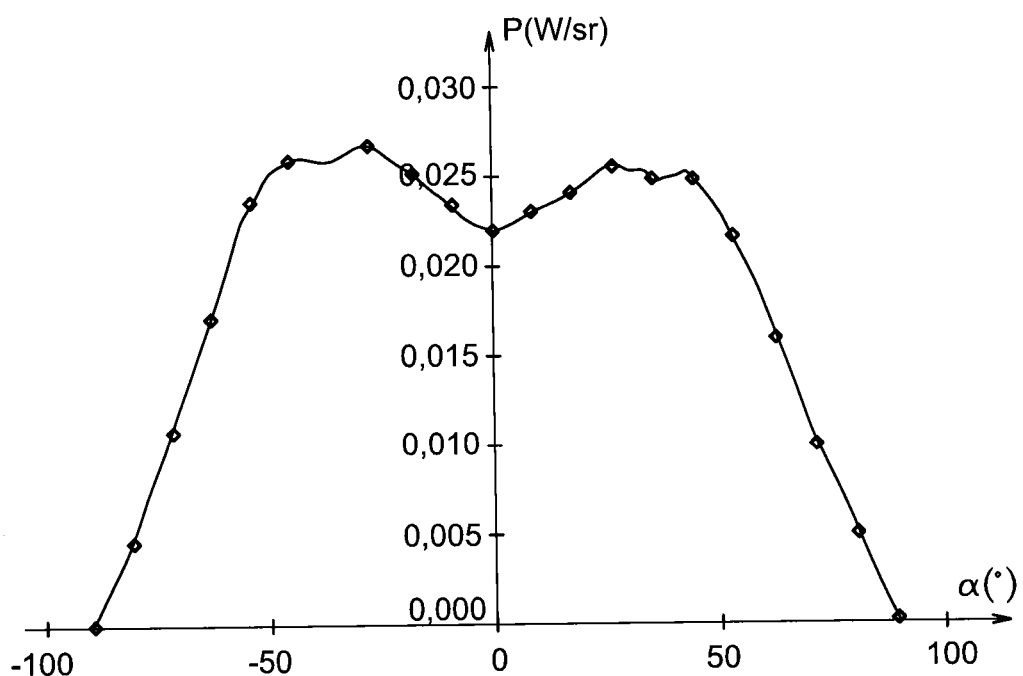
FIG. 8 shows the angular distribution of the light emission of a light emitting diode of Luxeon® III Emitter Lambert LXHL-PM09 type.

FIG. 8 shows, by way of example, the angular distribution of the light emission of a light emitting diode of Luxeon® III Emitter Lambert LXHL-PM09 type, in other words the variations in the optical power P emitted by said diode (in watts per steradian), as a function of the emission angle α (in degrees).

Various examples of the invention will now be given. In these examples, the invention is implemented with a source emitting a light beam that is not collimated: the light rays of said beam are not parallel to each other.

Nevertheless, the invention may be implemented with a primary source of light that emits a collimated light beam: it then suffices to make said beam divergent by means of an appropriate optical means, for example a divergent lens, or to implement a scatterer in the path of the collimated beam.

It is then considered that the invention is implemented with a light source constituted of said primary source and said optical means.

The examples of the invention, which are given hereafter, relate to a device for lighting an object, of the kind of that which has been described with reference to FIGS. 3A and 3B.

The same references have thus been used again to designate the same components. And the object to be lit is a sensor material, exposed to a sample that it is wished to analyse.

"Sensor material" is taken to mean a material, the optical properties of which are capable of evolving when it is placed in contact with an analyte. Thus, when a fluid, for example a gas or a liquid, flows in contact with the dot provided with the sensor material, and that the fluid comprises an analyte to which the sensor material is sensitive, the dot, thanks to the sensor material that it contains, undergoes a modification of its optical properties.

"Modification of the optical properties" is taken to mean an emission of a fluorescence light, a change of colour, a modification of the absorption.

The sensor materials may be porous polymers or sol-gels, for example described in the patent application WO 2007/031657, and in the article of R. Dagnelie et al., "Méthodes de mesure du formaldéhyde dans l'atmosphère", Revue Air Pur No 74, pages 14-21.

It will be noted that the invention applies just as well whether the dot comprising the sensor material is volumic and not surfacic.

Figure 9A:
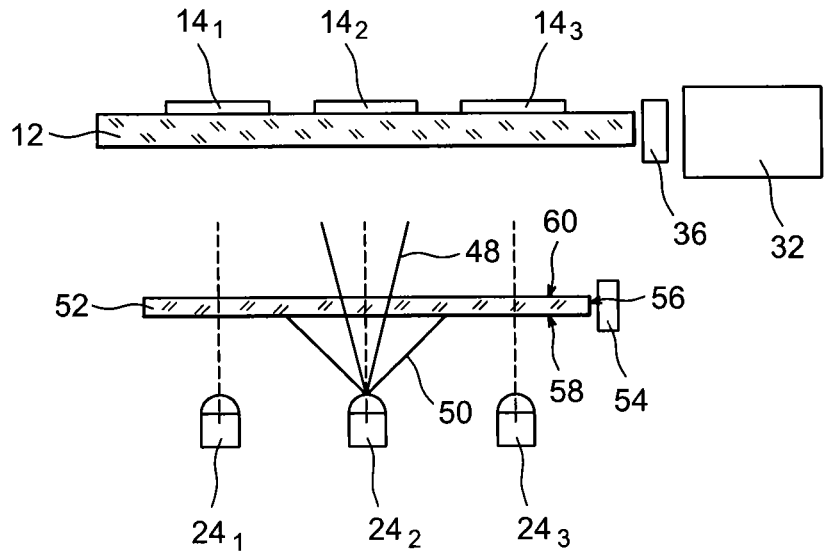
FIG. 9A is a schematic view of a particular embodiment of the device, the subject matter of the invention, which comprises a single plate with parallel faces as light sampling member, and wherein the light used for lighting an object is surrounded by the light that is not used for the lighting.

In FIG. 9A is thus represented, in a schematic and partial manner, a particular embodiment of the device, the subject matter of the invention. It comprises identical luminous sources $24_1$, $24_2$, $24_3$ for lighting respectively the sensitive materials $14_1$, $14_2$, $14_3$.

Said materials are placed on the plate with parallel faces 12 which is transparent to the light emitted by the sources. In the particular and non limiting case of a fluorescent sensor material, when the latter is exposed to a sample to be analysed and receives the light of the corresponding source, it emits a fluorescence radiation. The latter propagates in the plate 12 and it is detected by the photodetector 32 after having been filtered by the wavelength filter 34.

In the following, a focus will be made simply on the source $24_2$ and on the corresponding object $14_2$.

Said source $24_2$ is such that the light emitted by it comprises two parts: a first part 48, which is central in the example, and a second part 50, which is peripheral.

The first part 48 is used for lighting the object $14_2$ and the second part 50 is not used for lighting it.

According to the invention, the device of FIG. 9A moreover comprises a member 52 to sample at least one portion of the second part 50 of the light emitted by the source $24_2$. In other words, said member is arranged upstream of the object. "Upstream of the object" is taken to mean that it is situated on the path of the optical beam generated by the source, before the latter reaches the object. In this way, the light deviated by said member is essentially the light generated by the source. The function of said sampling member is of deviating part of the light generated by the source.

In this first example, said sampling member 52 is a simple plate with parallel faces that is transparent in the spectral domain to which belongs the light emitted by the source $24_2$.

Purely as an indication and in no way limiting, said spectral domain ranges from 100 nm to 5 μm.

The plate 52 is placed between the source $24_2$ and the object $14_2$ (between the set of sources $24_1$, $24_2$, $24_3$ and the plate 12 in the example represented), in a region where the second part 50 of the light emitted by the source $24_2$ propagates.

The plate 52 is for example made of glass. It is preferably thick, with a thickness comprised in the interval ranging from 50 μm to 5 mm. It is even preferable that this thickness is comprised in the interval ranging from 500 μm to 2 mm.

Apart from deviating the light produced by the source, the plate serves as light guide, to guide the portion of light deviated beforehand.

The device schematically represented in FIG. 9A moreover comprises a photodetector 54 for capturing at least one portion of the light sampled (or deviated), then guided, by the plate with parallel faces 52, supplying a signal representative of the flux of the light emitted by the source $14_2$, and thus making it possible to measure the variations of the flux (using appropriate means, not represented, provided for processing said signal).

As may be seen, the photodetector 54, or reference sensor, is placed facing one of the sides, or edges, of the sheet 52 (whereas the central part 48 of the light of the source $24_2$ traverses successively the lower face 58 and the upper face 60 of the plate 52 to go and light the object $14_2$).

Figure 9B:
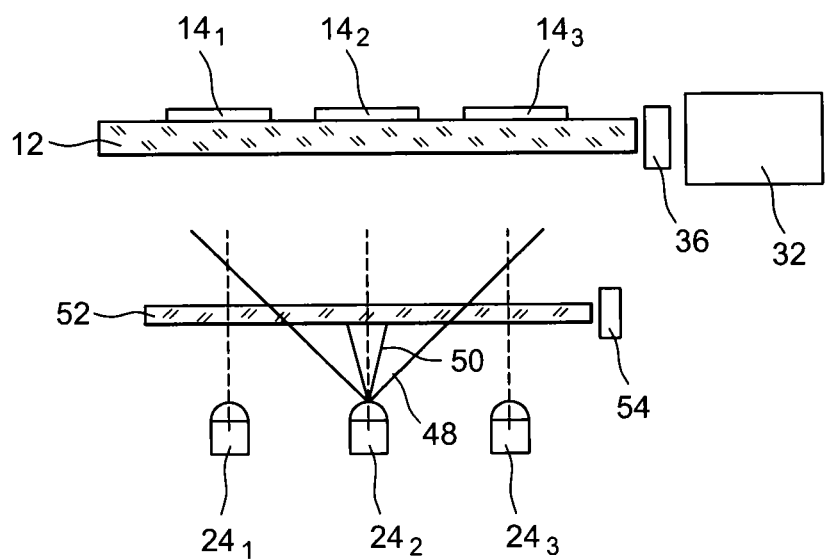
FIG. 9B is a schematic view of another particular embodiment, wherein the light used for lighting an object surrounds the light that is not used for the lighting, FIGS. 10 to 13 schematically illustrate various places possible for the light sampling member, in a device conforming to the invention.

FIG. 9B schematically illustrates the case where the source $14_2$ is such that the two parts of the light emitted by it are inversed with respect to the source that has been described with reference to FIG. 9A: in the example of FIG. 9B, the part 48 of said light, used for lighting the object $14_2$, is peripheral, whereas the part 50, which is not used for lighting the object, is central.

Figure 1:
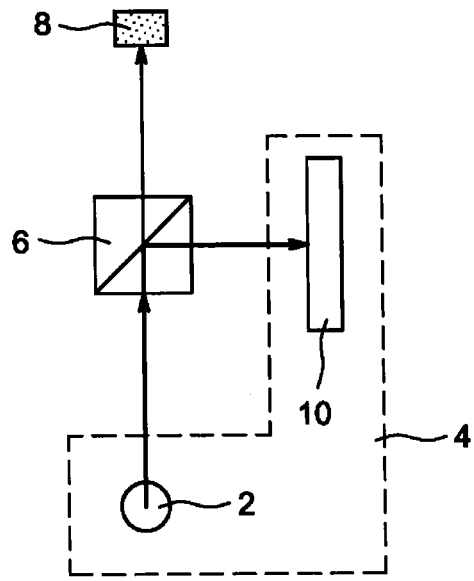
FIGS. 1 and 2 are schematic views of known devices for measuring the variations of the flux of a light source, and have already been described.
Figure 2:
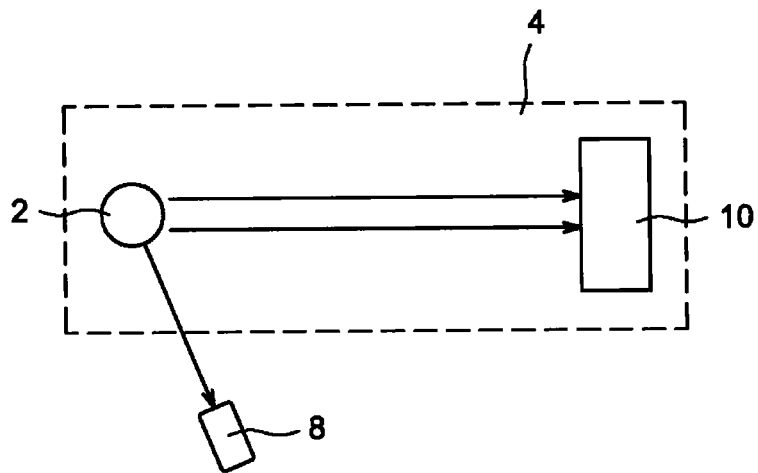
Figure 3A:
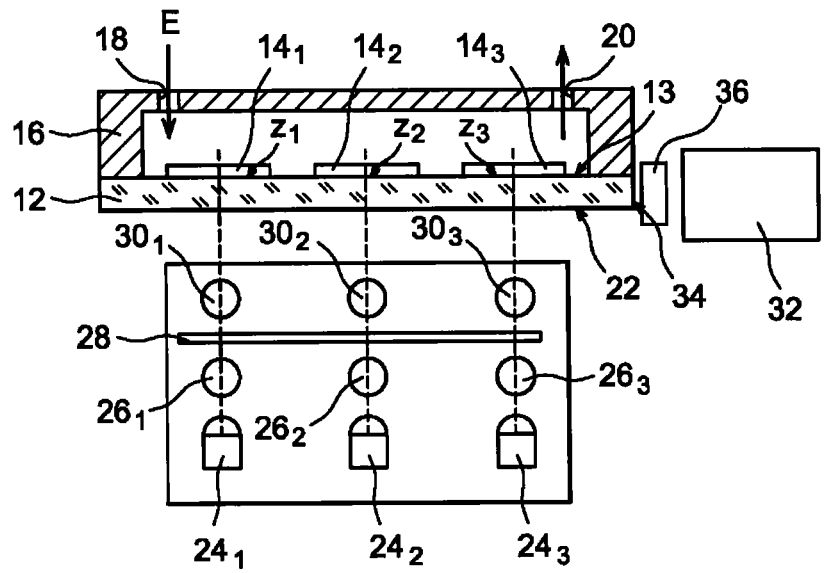
FIG. 3A is a schematic sectional view, and FIG. 3B a schematic top view, of a device for detecting and assaying biological or chemical substances, contained in a liquid or a gas, and have already been described, FIGS. 4 to 7 schematically illustrate various techniques for sampling a portion of the flux of each source that the device of FIGS. 3A and 3B comprises, and have already been described.
Figure 3B:
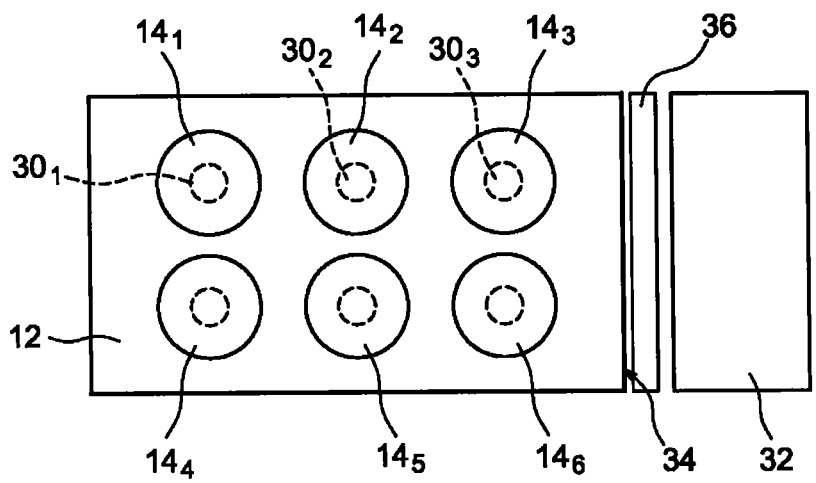
Figure 4:
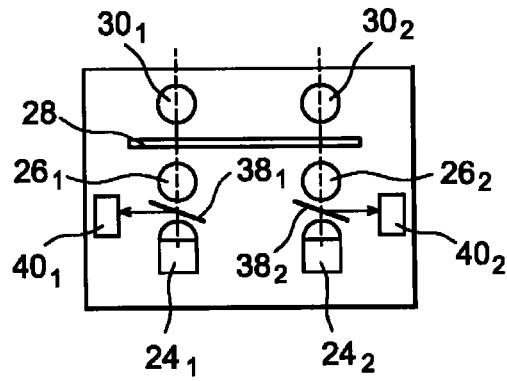
Figure 5:
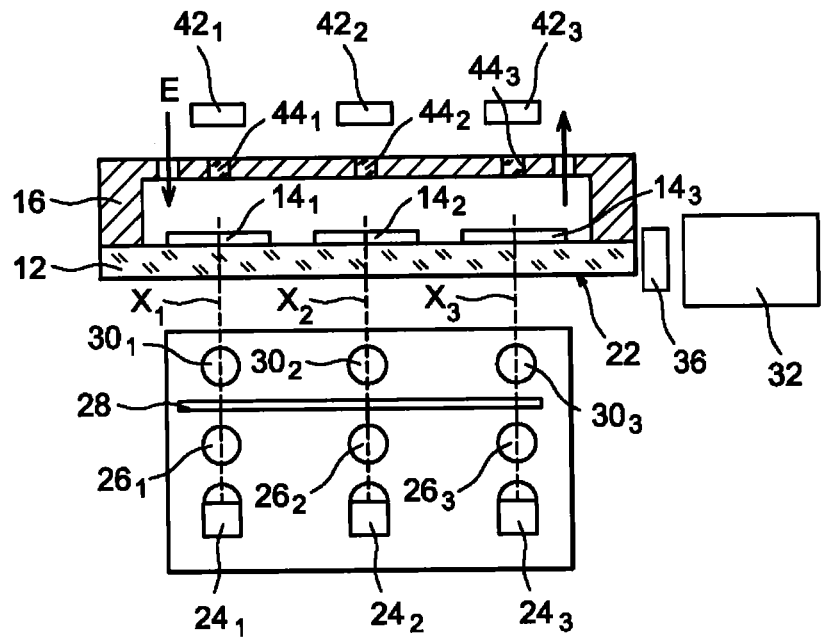
Figure 6:
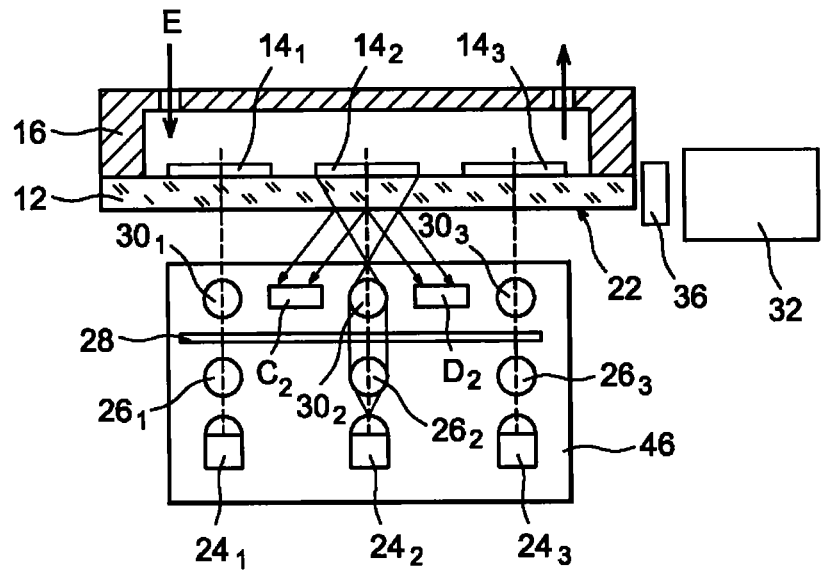

FIGS. 10, 11, 12 and 13 schematically illustrate various examples of the invention in which the light sources, in particular the source $24_2$, are provided with the optical system for shaping light, as mentioned in the description of the FIGS. 3A and 3B.

It will be recalled that said optical system comprises successively, from the set of light sources and for each one thereof, in particular the source $24_2$: the first lens $26_2$, the wavelength filter 28 and the second lens $30_2$.

Figure 11:
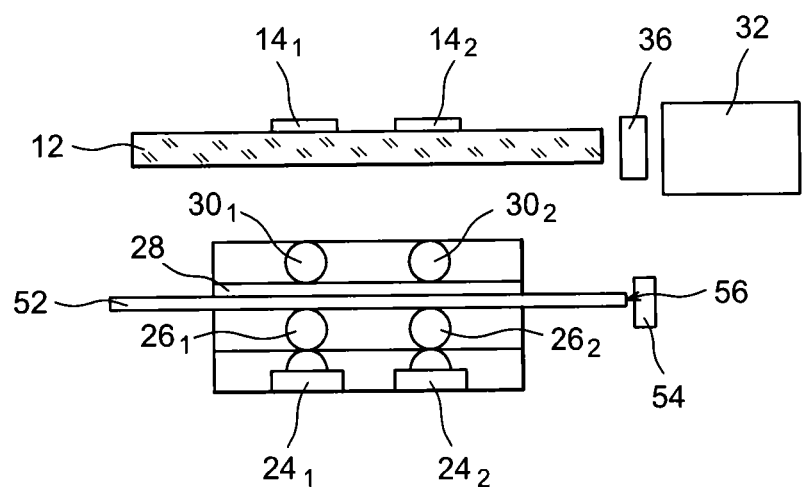
Figure 12:
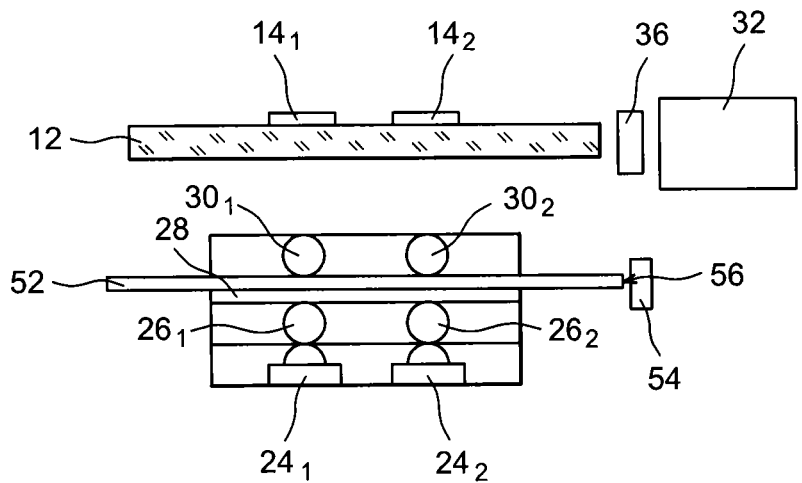
Figure 13:
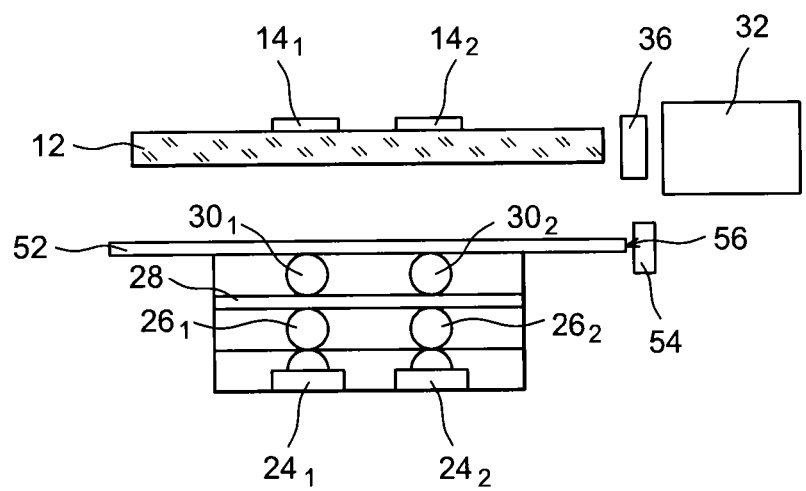

In the examples schematically illustrated by FIGS. 10 to 13, the plate with parallel faces 52 is arranged:
either between the set of light sources, in particular the source $24_2$, and the first lenses, in particular the lens $26_2$ (FIG. 10),
or between the first lenses and the wavelength filter 28 (FIG. 11),
or between the wavelength filter 28 and the second lenses, in particular the lens $30_2$ (FIG. 12),
or behind the second lenses, in particular the lens $30_2$, before the plate 12 (FIG. 13).

It has been shown experimentally that the position of the plate 52 is important: as has been seen, it is necessary to place said plate 52 in a region where the part of light not used 50 (FIGS. 9A and 9B) propagates and may thus be deviated, by a sampling member, then be guided in the direction of a photodetector.

Figure 10:
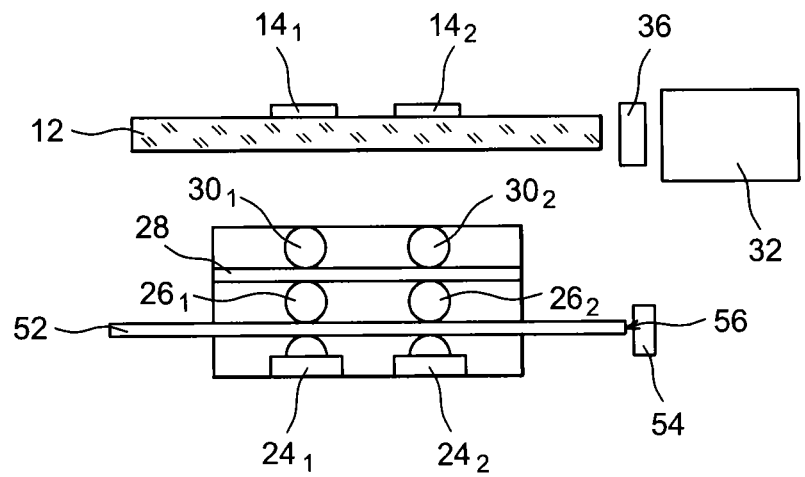

For the configurations represented in these FIGS. 10 and 11, the relative uncertainties for a measurement, calculated from the equation (5), are respectively equal to 0.3% and 2.72%.

These results show that the choice of the position of the sampling member is important: the layout of a plate of glass, shown in FIG. 10, makes it possible to collect the light emitted by the sources $24_1$, $24_2$ below the collection cone of the lenses $26_1$, $26_2$; whereas in the configuration illustrated by FIG. 11, said light is not transmitted by the lenses $26_1$, $26_2$ and it is lost for the measurements.

The particular embodiment represented in FIG. 12 makes it possible to take account of the spectral drifts of the light sources.

Nevertheless, in the case of FIG. 12, the luminous flux is lower than the flux measured in the configuration of FIG. 11 because an important fraction of the light is blocked by the filter 28. The measurement uncertainty is then greater and the correction of the variations of the intensity of the illumination produced by a source is more difficult to perform.

Moreover, in the case of FIG. 12, the photodetector 54 may be a simple photodetector, or a photodetector provided with a filter, or a colour sensor, or even a spectrophotometer.

The particular embodiment that is represented in FIG. 13 also makes it possible to take account of the spectral drifts of the light sources.

A preferred embodiment of the invention is considered hereafter, which makes it possible to couple more light in the plate with parallel faces. As has been seen, in fact, the greater the quantity of light coupled in said plate with parallel faces, the greater the measurement precision.

This preferred embodiment makes it possible, among others, to place the sampling member as is shown in FIG. 10: upstream of the filter 28 and the lenses $30_1$, $30_2$.

In an advantageous manner, according to all of the embodiments, to increase the fraction of light coupled in the plate, in the lighting device, a plate is used with parallel faces 62 (FIGS. 14A, 14B, 15A, 15B) comprising, for each source, a light scattering area, or light scatterer, able to deviate a part of the light that is emitted by the source, in the light guide. It is possible for example to deviate a part of the light that is not used for lighting the object.

In the examples that follow, said light scattering area, also known as "scatterer", is a scattering surface.

Figure 14A:
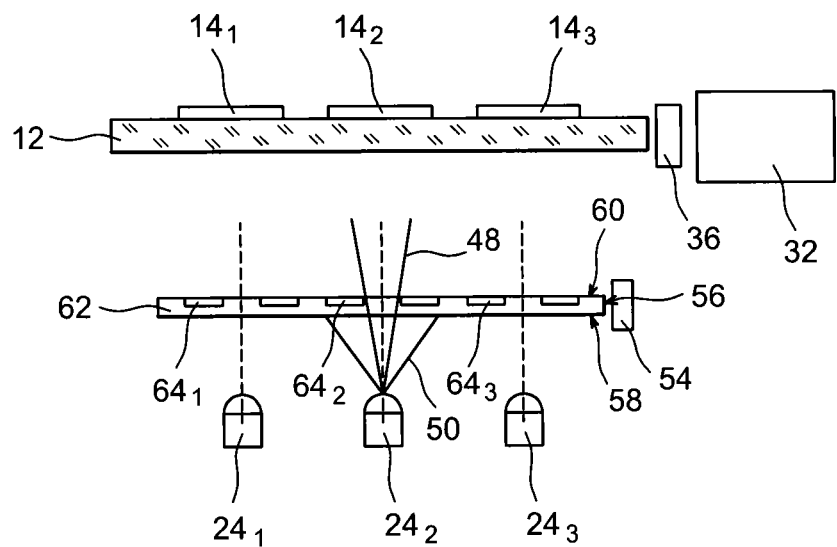
FIG. 14A is a schematic view of a preferred embodiment of the device, the subject matter of the invention, wherein the sampling member is a plate with parallel faces comprising annular light scattering areas.

The example illustrated by FIG. 14A is deduced from the example illustrated by FIG. 9A by replacing the plate 52 by the plate 62, which may be seen in FIG. 14A. And FIG. 14B is a top view of said plate 62.

Figure 15A:
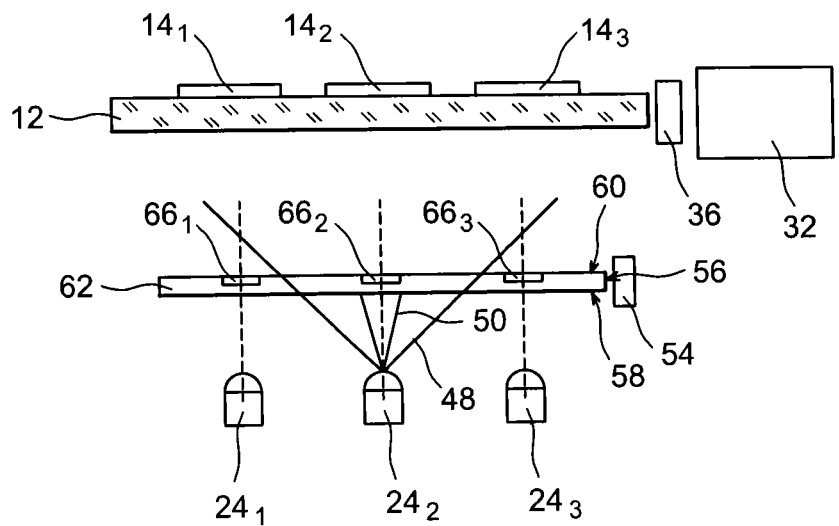
FIG. 15A is a schematic view of another preferred embodiment, wherein the sampling member is a plate with parallel faces comprising discoidal light scattering areas.

Similarly, the example illustrated by FIG. 15A is deduced from the example illustrated by FIG. 9B by replacing the plate 52 by the plate 62, which may be seen in FIG. 15A. And FIG. 15B is a top view of said plate 62.

Figure 14B:
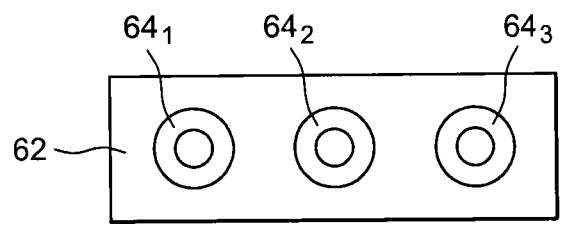
FIG. 14B is a schematic top view of said sampling member.

In the example schematically illustrated by FIGS. 14A and 14B, the second part 50 of the light emitted by a source such as the source $24_2$ surrounds the first part 48, and each scattering surface has the shape of a ring. The annular scattering surfaces, associated with the sources $24_1$, $24_2$, $24_3$, have respectively the references $64_1$, $64_2$, $64_3$.

Figure 15B:
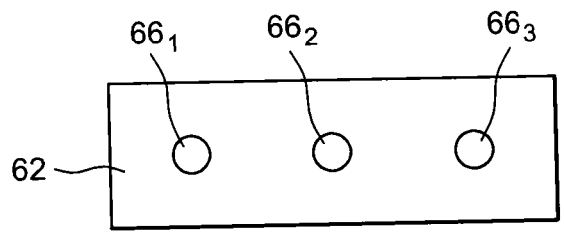
FIG. 15B is a schematic top view of said sampling member, FIG. 16 schematically illustrates the principle of the deviation of the light rays by a scatterer of the kind of light scattering areas that the plate of FIGS. 15A and 15B comprises.

In the example schematically illustrated by FIGS. 15A and 15B, the first part 48 of the light emitted by a source such as the source $24_2$ surrounds the second part 50, and each scattering surface has the shape of a disc. The disc shaped scattering surfaces, associated with the sources $24_1$, $24_2$, $24_3$, have respectively the references $66_1$, $66_2$, $66_3$.

Typically, the surface of a scatterer may be comprised between 0.5 and 10 times the surface area formed, on the plate, by the beam incident to the illuminated object, and preferably between 0.5 and 5 times.

The external perimeter of a scatterer may be circular or polyhedral. Similarly, when the scatterer is a ring, the internal perimeter of the ring may be circular or polyhedral.

Preferably, whatever the embodiment, the scatterers are constituted of superficial rough areas of the light guide, the arithmetic roughness of which is comprised in the interval ranging from 100 nm to 50 μm. This makes it possible to favour the elastic scattering of the light with respect to the phenomenon of diffraction.

In other words, with such a roughness, the deviation of the light in the guide takes place mainly by elastic scattering. This constitutes a simpler solution compared to the use of diffraction gratings. Thus, "scatterer" is taken to mean an element able to deviate, by scattering, a light that it receives.

Figure 16:
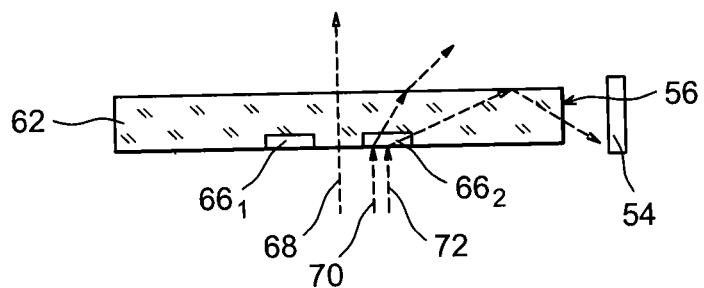

FIG. 16 schematically illustrates the principle of the deviation of light rays by a scatterer of the kind of scattering surfaces $66_1$, $66_2$ of the plate of glass 62 of FIGS. 15A and 15B.

The light rays are emitted by the source (not represented) that is associated with said scatterer.

After deviation by a scatterer, a portion of the light is trapped in the glass plate 62 and propagates therein by total internal reflection if its incidence, in the plate, is greater than the critical angle of total reflection defined hereafter. In other words, the plate acts as light guide, or wave guide.

Then, said portion of light emerges by the side 56 of the plate 62 and it is captured by the photodetector 54.

For example, the light ray 68 does not encounter any scatterer and its direction is not modified; it traverses the plate 62 and exits via the face opposite to the inlet face.

The light ray 70 encounters the scatterer $62_2$ but its refraction is insufficient in order that its angle, after the input face, is greater than the critical angle of total reflection $\theta_c$. Thus, the light ray 70 also traverses the plate 62 exiting by the face opposite to the inlet face.

It should be recalled that the angle $\theta_c$ is defined by the following formula:

$$\theta_c = \arcsin(n_2/n_1)$$

where $n_1$ designates the refractive index of the plate and $n_2$ the refractive index of the medium surrounding said plate.

The light ray 72 encounters the scatterer $62_2$ and its refraction is sufficient so that its angle, after the input face, is greater than the critical angle of total reflection $\theta_c$. Said ray 72 is coupled in the plate 62 and emerges by the side 56 thereof. It is then captured by the photodetector 54 which is arranged facing said side 56.

The shape and the geometric parameters of each scattering surface are defined according to, on the one hand, the directivity of the associated light source and, on the other hand, the quantity of coupled light, required to carry out a precise reference measurement.

The quantity of light that is coupled thanks to a scattering surface is also a function of the roughness of said surface. Said roughness, expressed as the arithmetic roughness, noted Ra, depends on the technique of manufacturing the scattering surface.

For example, the roughness of a glass surface, of microscope plate type, is equal to around 2 nm; it is much smaller than the wavelengths of the lights used in an example of the invention for lighting the interrogation areas as mentioned above; and such a surface does not scatter enough light for the measurements to be exploitable.

For example, in the visible domain, with a wavelength λ of 500 nm, a roughness Ra of 2 nm, and a plate made of borosilicate glass, having a refractive index $n_1$ equal to 1.523 and placed in the air (of which the refractive index $n_2$ is equal to 1), it is found that the total coupled intensity $I_c$ in the plate is equal to 0.01% of the intensity $I_o$ of the incident light. In this respect, reference will be made to the following document:

[2] J. M. Elson et al., "*Relationship of the total integrated scattering from multilayercoated optics to angle of incidence, polarization, correlation-length, and roughness crosscorrelation properties*", Appl. Opt., 22, 3207 (1983)).

To determine $I_c$, the following formulas are used:

$$R = \left[\frac{n_1 - n_2}{n_1 + n_2}\right]^2 = 0.04$$

$$D = R\left[\frac{4\pi Ra}{\lambda}\right]^2 \approx 10^{-4}$$

$$I_C = D \times I_0$$

where R designates the reflection factor and D the scattering factor.

Advantageously, the surface is thus rendered scattering by increasing the roughness Ra, according to the desired value, by different techniques which are described hereafter, so as to obtain a superficial rough area, the roughness Ra of which is greater than the wavelengths of the spectral domain to which belongs the light emitted by the corresponding source.

To be efficient, it is preferable that this roughness Ra is comprised between 100 nm and 50 μm.

For example, it is possible to form, by microbead blasting, scatterers in the form of rings of the kind of those shown in FIG. 14B. Then, by placing the plate provided with said diffusing rings as shown in FIG. 10, on the side 56 of the plate, an illumination equal to 9.3 W/m² is obtained; whereas the illumination without diffusing surface, for a plate at the same position, is equal to 0.064 W/m².

The gain in measurable flux is then of the order of 150. This leads to a measurement uncertainty of 0.02% instead of 0.30%, keeping the same hypotheses as previously.

Figure 17A:
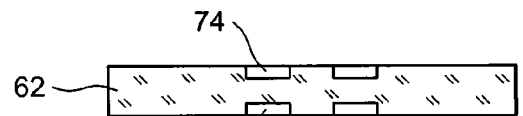
FIGS. 17A and 17B are schematic views of a plate provided with scattering rings formed facing each other (FIG. 17A: symmetrical rings—FIG. 17B: dissymmetrical rings)
Figure 17B:

To further increase the quantity of coupled light, it is possible to form two scatterers facing each other, which are either symmetrical (FIG. 17A), or dissymmetrical (FIG. 17B).

More precisely, in the example of the invention which is schematically and partially illustrated by FIG. 17A, the plate with parallel faces 62 comprises, for each light source, two annular scattering surfaces 74, 76 which are identical and are respectively situated facing each other, on two opposite faces of the plate with parallel faces. Thus, the plate with parallel face acts on the one hand as sampling member of the light emitted by the source, on the other hand as light guide of the light thereby sampled.

And, in the example of the invention which is schematically and partially illustrated by FIG. 17B, the plate with parallel faces 62 comprises, for each light source, two annular scattering surfaces 78, 80 which are different and are respectively situated facing each other, on two opposite faces of the plate with parallel faces.

The choice between these two configurations is made according to the expected results, the type of source used for the illumination and the shaping of the light beam emitted by said source.

Figure 18:
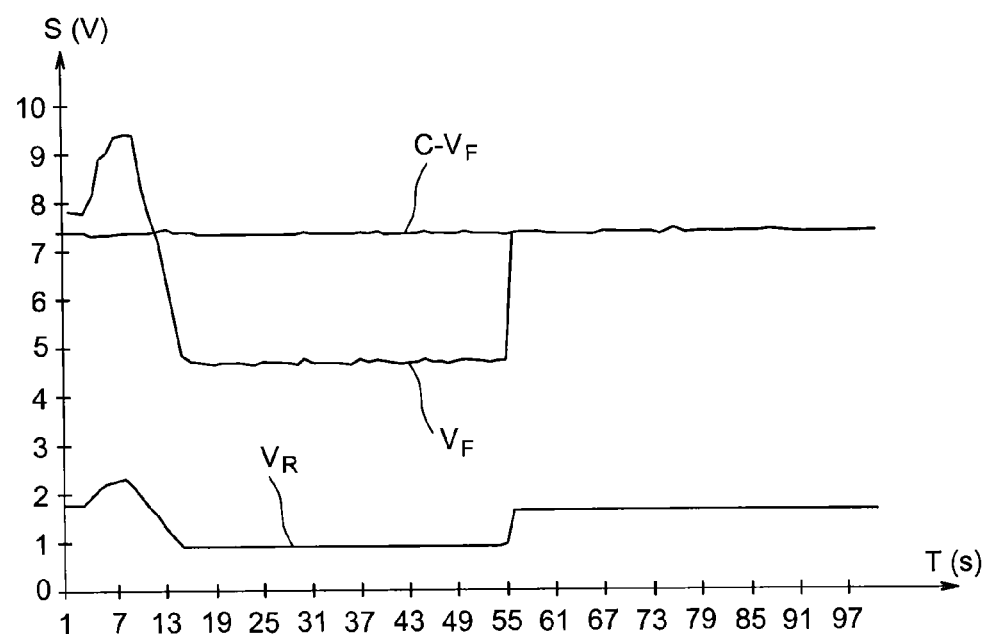
FIG. 18 shows the correction applied to a luminous signal of excitation of interrogation area, which varies over time.

FIG. 18 is an illustration of experimental results that have been obtained. More precisely, it shows the correction applied to a luminous signal of excitation of interrogation area, which varies over time. The black signals are not represented.

In FIG. 18, the time T (in seconds) is given on the abscissa and the measured signals S (in volts) are given on the ordinate.

Figure 7:
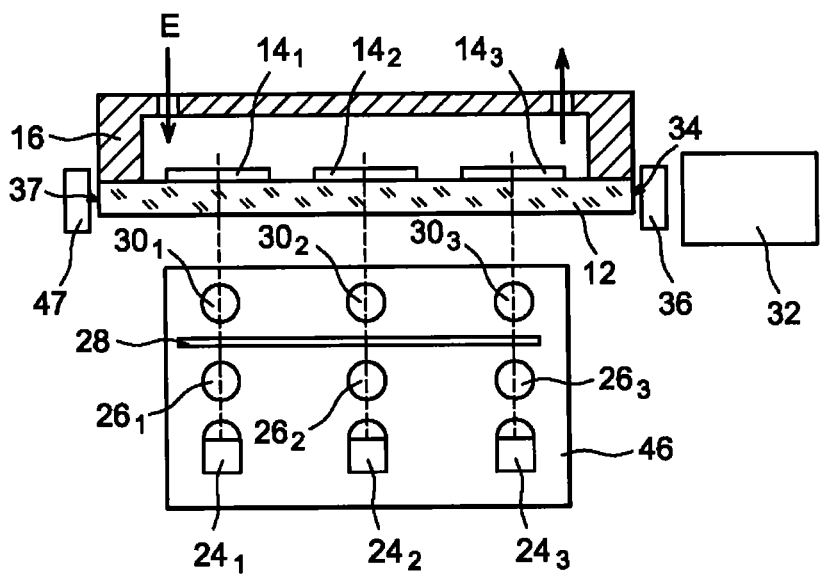

This figure makes it possible to compare a non corrected fluorescence measurement, obtained with the photodetector 32 (FIG. 7), with a fluorescence measurement again obtained with said photodetector, but corrected by means of the photodetector 54 and the sampling member which may be seen in FIG. 14A.

A procedure for carrying out this correction is given hereafter.

During the reading of a sensitive material, four measurements are made, or four average measurements, of the signals respectively from the fluorescence sensor (photodetector 32) and the reference sensor (photodetector 54):

measuring the black signal of the reference sensor (the light sources are switched off): $O_R$,
measuring the black signal of the fluorescence sensor (the light sources are switched off): $O_F$,
measuring the signal supplied by the reference sensor: $V_R$,
measuring the signal supplied by the fluorescence sensor: $V_F$.

The correction method used is described hereafter.

Step 1
At the start of the experiment, the reading is performed of the sensitive material considered;
four measurements are obtained: $O_{R0}$, $V_{R0}$, $O_{F0}$, $V_{F0}$;
a correction factor Cf is then calculated; it is given by the following formula:

$$Cf = \frac{V_{F0} - O_{F0}}{V_{R0} - O_{R0}}.$$

Step 2
During an interrogation cycle, for each sensitive material, the signals $O_R$, $V_R$, $O_F$, $V_F$ are measured.

Step 3
The corrected fluorescence measurement C_VF is given by the following formula:

$$C\_V_F = Cf \times (V_R - O_R) - O_F$$

This procedure is applied to the signals represented in FIG. 18.

On the photodetector 32, a raw signal is measured which shows a strong variation of amplitude. Said photodetector 32 enables the signals $O_F$ and $V_F$ to be measured.

Simultaneously, a reference signal is measured from light rays deviated by an annular scatterer such as the scatterer $64_1$ of FIG. 14A. The intensity of this signal is measured by the reference sensor 54 which makes it possible to acquire the reference signals $O_R$ and $V_R$.

By applying the method described above, the corrected measurement signal C_VF is obtained. Said signal is corrected by means of a comparison of the measurement detected by the photodetector 32 with the signal detected by the reference photodetector; this comparison appears here in the form of a ratio. Naturally, any other arithmetic combination expressing a comparison between two signals (particularly subtraction) could be used, the general idea being to compare the intensity of the signal measured with the intensity of the signal incident to the sample.

Returning to the embodiment of the invention, in which a single plate with parallel faces is used, placed in a region making it possible to recover a sufficient portion of the light that is not used for lighting the studied object.

The plate must be made of a material that is transparent in the spectral domain of the light source. For the visible domain, the material may be, for example, glass, silica, or a synthetic material (for example PMMA or polystyrene).

If it is necessary to limit the light to a reduced spectral interval, the plate may be placed after a wavelength filter, as shown in FIG. 12.

To increase the quantity of coupled light in the plate, and if the selection constraints of the spectral interval so allow, the filter may be placed between the source (or the sources in the case of FIG. 12) and the sampling plate 62.

Generally speaking, all of the combinations of relative layouts of the sources, lenses, filter (or even filters) and the sampling plate may be envisaged according to the sources and the lenses used and according to the envisaged applications. Therefore the examples given are not restrictive.

Let us return now to the preferred embodiment of the invention, wherein a scattering surface is used to intercept the part of the light that is not used for lighting the object.

Numerous methods exist for forming a scattering surface from a smooth surface.

It is possible to roughen said smooth surface by a chemical attack, for example by means of hydrofluoric acid, ammonium bifluoride or hydrochloric acid. The action of these acids may be localized, by depositing, on the plate of which it is wished to roughen the surface, drops of such acids at the places where it is wished to create roughened areas.

A milling by means of a diamond cutter also makes it possible to obtain a scattering surface, as does an erosion with ultrasounds, using a tool, the shape of which corresponds to the requisite pattern.

It is also possible to roughen the surface using a liquid, containing suspended particles, and a tool of suitable shape.

It is also possible to carry out a microbead blasting of the surface after having protected the parts thereof that it is not wished to roughen.

An example of this latter method is described hereafter.

Firstly a mask is formed to protect the regions that it is not wished to roughen. Said mask may be made using an adhesive film (for example of Arcare 90106 type, commercialized by the company Adhesive Research) which will be removed after the microbead blasting. The cutting may be carried out with a specialized robot (for example of Craft Robo Pro E5000 type, commercialized by the company Graphtec).

The mask is then positioned on the glass plate with which it is wished to form the sampling member.

The microbead blasting may be carried out with a workshop sandblaster and small glass beads. The diameter of the beads and the projection conditions (pressure of the sand jet, exposure time) define the roughness that will be obtained for the surface. After the projection, the mask is removed and the plate is cleaned with a suitable solvent, for example ethanol, acetone or isopropanol.

It is also possible to stick diffusing and transparent films on the areas of the surface where it is wished to form the scatterers, for example films made of a polyester such as polyethylene terephthalate or PET, which are semi-transparent and pearly.

Numerous scatterers, developed for lighting, are also commercially available.

It is also possible to obtain a deviation of the light rays in the chosen regions of the plate 62, through the intermediary of micro-prisms or Fresnel lenses, formed by embossing in said regions, for a transparent plate that is made of a synthetic material such as PMMA or polystyrene.

In a variant, a film comprising microprisms and a Fresnel lens structure may be stuck to the plate. Numerous products of this kind, developed for lighting, are commercially available.

Obviously, the present invention does not apply only to a device of the kind of that which is described in the document [1].

In addition, it is not limited to the measurement of flux variations of a light source.

The present invention applies to any device for lighting an object, device from which it is wished to sample a portion of the emitted light, whatever the envisaged use for this portion.

And the object to be lit is not limited to a sample that it is wished to analyse: the invention applies to any domain in which there is a need to light an object of whatever nature, even a living being or a scene.

The invention claimed is:

1. A device for lighting at least one object, comprising:
    at least one light source emitting an illuminating light around a illumination axis;
    a means for sampling and guiding light, arranged upstream of the object, said means for sampling and guiding light being able to deviate and guide a part of said illuminating light;
    a first photodetector for receiving the light transmitted by the object under the effect of the illumination;
    a reference photodetector for receiving the light guided by the means for sampling and guiding light; and
    a means for processing the signal supplied by the first photodetector by means of the signal supplied by the reference photodetector,
    wherein the light source is provided with an optical system for shaping the emitted light, said optical system comprising successively, from the light source, a first lens, a wavelength filter and a second lens, and
    wherein the means for sampling and guiding light comprises a plate with parallel faces, which is transparent in the spectral domain of the illuminating light, said plate being arranged in one of the places chosen among:
        a place between the light source and the first lens,
        a place between the first lens and the wavelength filter,
        a place between the wavelength filter and the second lens, and
        a place behind the second lens.

2. The device according to claim 1, wherein the means for sampling and guiding light is oriented perpendicularly to the lighting axis, so as to guide the light deviated perpendicularly to the lighting axis.

3. The device according to claim 1, wherein the thickness of the plate with parallel faces is comprised in the interval ranging from 50 μm to 5 mm, preferably from 500 μm to 2 mm.

4. The device according to claim 1, further comprising a support for the at least one object, the support having at least one side, wherein the support is transparent to the illuminating light, the first photodetector is placed in front of one of the sides of the support, and the light transmitted by the object propagates in the support and is detected by the first photodetector.

5. A device for lighting at least one object, comprising:
    at least one light source emitting an illuminating light around a illumination axis;
    a means for sampling and guiding light, arranged upstream of the object, said means for sampling and guiding light being able to deviate and guide a part of said illuminating light;
    a first photodetector for receiving the light transmitted by the object under the effect of the illumination;
    a reference photodetector for receiving the light guided by the means for sampling and guiding light; and
    a means for processing the signal supplied by the first photodetector by means of the signal supplied by the reference photodetector,
    wherein the light source is provided with an optical system for shaping the emitted light, said optical system comprising successively, from the light source, a first lens, a wavelength filter and a second lens,
    wherein the means for sampling and guiding light comprises a plate with parallel faces, which is transparent in the spectral domain of the illuminating light, said plate being arranged in one of the places chosen among:
        a place between the light source and the first lens,
        a place between the first lens and the wavelength filter,
        a place between the wavelength filter and the second lens, and
        a place behind the second lens, and
    wherein the plate with parallel faces comprises at least one light scattering area, which is able to deviate the light emitted by the source such that the deviated light is guided by said plate with parallel faces.

6. The device according to claim 5, wherein the light scattering area has the shape of a ring.

7. The device according to claim 5, wherein the light scattering area has the shape of a disc.

8. The device according to claim 5, wherein the light scattering area is a superficial rough area of the plate with parallel faces.

9. The device according to claim 8, wherein the arithmetic roughness of the superficial rough area is greater than the wavelengths of the spectral domain to which belongs the light emitted by the source, and said arithmetic roughness is comprised in the interval ranging from 100 nm to 50 µm.

10. The device according to claim 5, wherein the plate with parallel faces comprises two light scattering areas which are identical and are respectively situated facing each other, on two opposite faces of the plate with parallel faces.

11. The device according to claim 5, wherein the plate with parallel faces comprises two light scattering areas which are different and are respectively situated facing each other, on two opposite faces of the plate with parallel faces.

12. A method for correcting an optical signal emitted by an object, comprising:
  lighting the object by means of a light source;
  detecting the light emitted by the object under the effect of the illumination by the light source, by means of a first photodetector;
  deviating the light emitted by the source, upstream of the illuminated object, by means of a light guide, the said light guide guiding the deviated light to a reference photodetector; and
  processing a signal produced by the first photodetector as a function of an optical signal detected by the reference photodetector,
  wherein the processing comprises correcting the signal produced by the first photodetector as the function of the optical signal detected by the reference photodetector.

* * * * *